(12) United States Patent
Meyer

(10) Patent No.: US 11,974,936 B1
(45) Date of Patent: May 7, 2024

(54) LUMBOSACRAL SUPPORT DEVICE, METHOD AND KIT

(71) Applicant: Sean Meyer, Ormond Beach, FL (US)

(72) Inventor: Sean Meyer, Ormond Beach, FL (US)

( * ) Notice: Subject to any disclaimer, the term of this patent is extended or adjusted under 35 U.S.C. 154(b) by 0 days.

(21) Appl. No.: 18/416,520

(22) Filed: Jan. 18, 2024

(51) Int. Cl.
*A61F 5/02* (2006.01)

(52) U.S. Cl.
CPC .............. *A61F 5/028* (2013.01); *A61F 5/024* (2013.01)

(58) Field of Classification Search
CPC .......... A61F 5/01; A61F 5/02–03; A61F 5/30; A61F 5/32; A61F 5/37; A61F 13/14; A61F 13/143; A61F 13/145; A61F 13/148; A41C 1/00; A41C 1/02; A41C 1/08–14
See application file for complete search history.

(56) References Cited

U.S. PATENT DOCUMENTS

| | | | |
|---|---|---|---|
| 3,578,773 A * | 5/1971 | Schultz | A61F 5/24 602/19 |
| 4,905,993 A * | 3/1990 | Barone | A61F 5/028 482/106 |
| 5,188,585 A * | 2/1993 | Peters | A61F 5/028 2/311 |
| 5,363,863 A | 11/1994 | Lelli et al. | |
| 5,433,697 A | 7/1995 | Cox | |
| 5,551,085 A | 9/1996 | Leighton | |
| 6,099,490 A | 8/2000 | Turtzo | |
| 7,329,231 B2 | 2/2008 | Frank | |
| 8,235,925 B2 | 8/2012 | Cavalieri | |
| D957,654 S | 7/2022 | Savchuk | |
| 11,617,669 B2 * | 4/2023 | Cebe | A61B 5/4836 606/201 |
| 2006/0206992 A1 * | 9/2006 | Godshaw | A61F 5/028 224/904 |
| 2009/0192425 A1 | 7/2009 | Garth | |
| 2017/0189758 A1 * | 7/2017 | Angulo | A61F 5/30 |
| 2020/0262056 A1 | 8/2020 | Riegger et al. | |

* cited by examiner

*Primary Examiner* — Michelle J Lee
(74) *Attorney, Agent, or Firm* — Lori Sandman, Esq.

(57) ABSTRACT

The present invention relates to devices for providing support to the lower back. Specifically, it discloses an improved back support device featuring a removable and replaceable lumbar support system capable of reconfiguration to supply support, compression and/or gentle pressure to the lumbar area of the body. Different sized or shaped inserts can be used to accommodate therapy and training, and to customize the device for individuals of all body shapes and sizes. The device and method disclosed are safe and effective for both training and rehabilitation, and advance the field of orthopedic and ergonomic support devices.

16 Claims, 5 Drawing Sheets

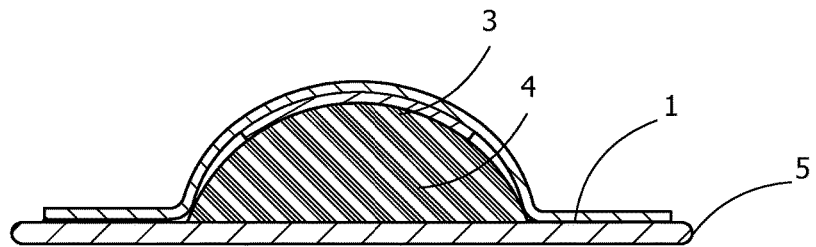
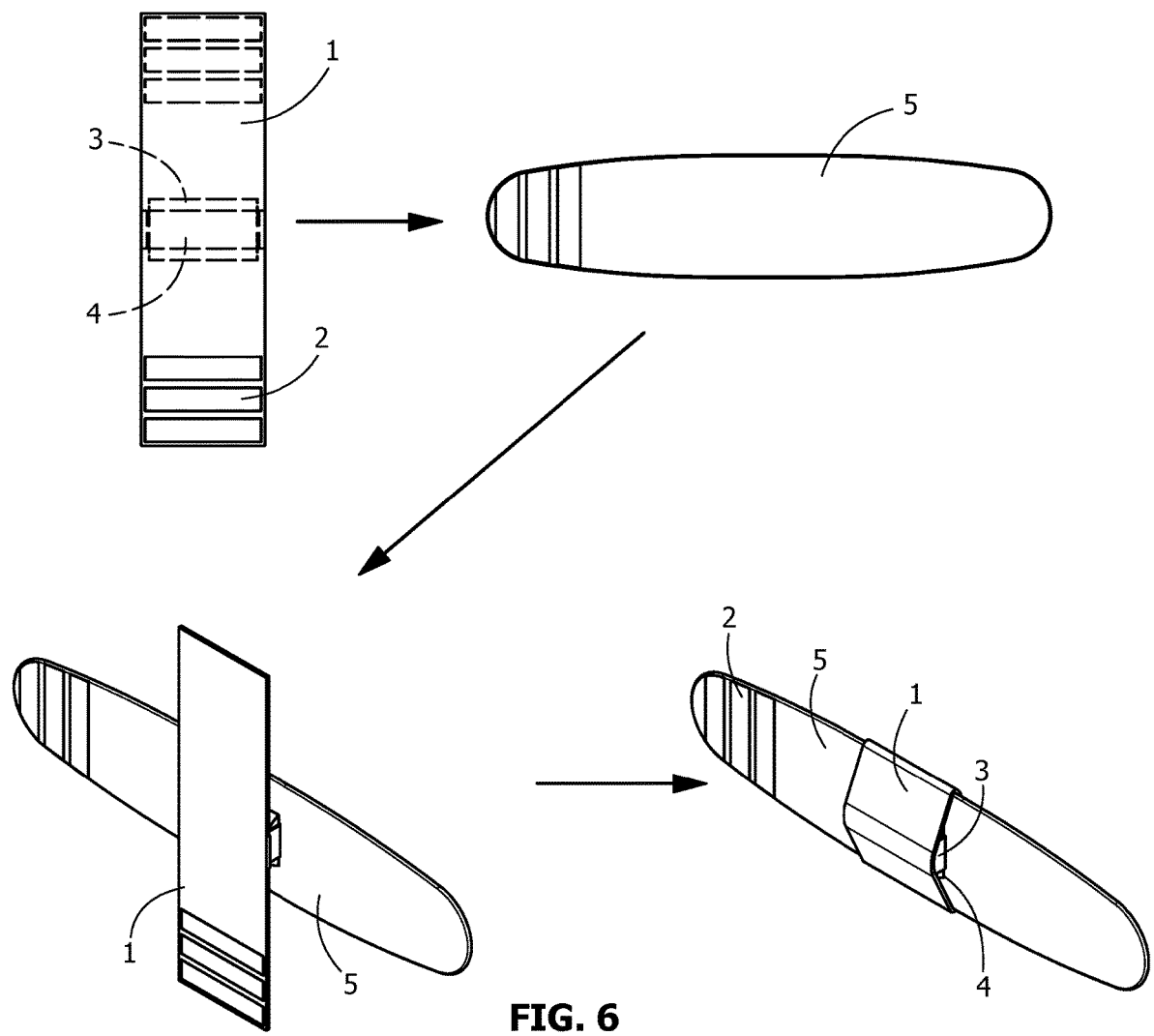

LUMBOSACRAL SUPPORT DEVICE, METHOD AND KIT

CROSS-REFERENCE TO RELATED APPLICATIONS

Not applicable.

STATEMENT REGARDING FEDERALLY SPONSORED RESEARCH/DEVELOPMENT

Not applicable.

REFERENCE TO SEQUENCE LISTING, A TABLE, OR COMPUTER PROGRAM LISTING COMPACT DISC APPENDIX

Not applicable.

BACKGROUND OF THE INVENTION

The present invention relates to orthopedic devices for providing support to the lower back. Specifically, it discloses a device, method of using the device and a kit for improved back support while exercising, working or doing other activity that may push the lumbar out of its natural curve. The device is comprised of a removable, adjustable and replaceable lumbar support system capable of reconfiguration to supply individualized support for a particular wearer, and can also provide gentle pressure to the lumbar area of the body to help support the body and maintain proper posture. The device is safe and effective for both training and rehabilitation and advances the field of orthopedic and ergonomic support devices.

The increase in sedentary jobs, time sitting in front of computer screens and trends in decreasing physical labor and activity have resulted in a concomitant increase in musculoskeletal disorders and back pain affecting people worldwide. Lower back pain can affect individuals of any age or occupation and can have a substantial impact on quality of life, work productivity, and healthcare costs.

Doctors, physiologists, therapists, and ergonomic experts have deployed various solutions to overcome back pain and support the lumbar and lower back. Back braces in a variety of configurations, lumbar pillows, and a spectrum of flexible and rigid supports have been used. Trends in personalized healthcare solutions have resulted in designs for wearable supports and belts that provide back bracing functions. However, a pressing need still exists for a device that can provide accurately placed support specifically for the lumbosacral region of the body during exercise, training, and rehabilitation.

BRIEF SUMMARY OF THE INVENTION

Today, advances in medical tools and wearable technology provide for new materials and innovative designs that impact new product development. Utilizing this new technology and materials, the present invention discloses a reconfigurable, wearable device that can be used with existing compatible weight training devices or supplied as a complete system and kit. The device and method of use allow the wearer to maintain the natural curvature of the lumbar spine during workouts and therapy or rehabilitation sessions. By maintaining the natural curvature of the lumbar spine, unnatural flexion that can lead to injury is prevented.

The device disclosed comprises a flexible and reflexive body wrap; a "stoling" used hereinafter to refer to a covering that encircles or retains an insert. The stoling includes at least a first side and a second side; a restraining strap capable of receiving and securing at least one lumbosacral insert; and one or more attachment bands capable of securing the stoling around or upon a wrap in order to position the lumbosacral insert across the lumbosacral region of a wearer's body to provide musculoskeletal support.

The restraining straps of the device engage with and are capable of receiving and securing at least one removable, non-collapsible lumbosacral insert. The system can include one or more specifically sized inserts, or a series of differently sized inserts designed for increasing back strength by changing support dimensions. The device, in combination with the method of use, assists the wearer in being conscious of good posture, reminding him or her when the lower back posture is beginning to slouch. The present device could also be worn for support while working in places or situations in which carrying and moving heavy objects could compromise healing or recovery, such as in places where people are lifting heavy loads, manual physical labor jobs such as landscaping, construction, operating heavy machinery, and related work. It could be used during rehabilitation in order to maintain proper curvature of the lumbar, especially after a lumbar injury or where not doing so could lead to further aggravation or injury. Furthermore, the device can be worn underneath or on top of clothing. The device is capable of providing a custom, comfortable fit so that a user can wear it throughout the day during regular activity. In this way, it helps the hips stay aligned so that weight can be equally and more comfortably distributed.

In a preferred embodiment, the insert is made out of relatively dense foam or similar material. One skilled in the art would appreciate that similar materials with similar material characteristics to foam would be appropriate and fall within this disclosure. This material, because of its physical makeup, naturally repels water which prevents it from absorbing and holding liquids, such as sweat, during a workout. The insert is relatively rigid, semi-circular including at least a rounded side or surface and a flat side or surface, and when in position on the body, extends perpendicular to the spine at the top of the plane of the hips, from hip to hip across the spine interacting with the musculature of the back. The material is firm enough to add support to the lumbar to help maintain good posture while exercising and working, but it maintains a slight flexion; it is capable of minor compression and expansion to allow for comfort when positioned against the body. This invention helps keep the hips even while helping to maintain the natural curve in the lumbar which can help prevent common back injuries and reaggravating or worsening a previous or current injury. A set of variously sized inserts allow for different physical needs.

One significant improvement of the present invention over related art includes increased support in the lumbar section. The device is capable of counteracting the force exerted by push-type exercises such as the leg press and other activity that can unnaturally curve the lumbar region. A single, variably sized insert is an advantage over devices that include multiple small flexible supports that are designed for constant use.

It is an object of this invention to provide a back support system that can be customized to suit an individual's unique body shape and needs, ensuring optimal support and comfort.

It is another object of this invention to provide a lumbosacral support device that allows the wearer to maintain the natural curvature of the lumbar spine during workouts and therapy or rehabilitation sessions.

It is one more object of this invention to add support to the lumbar region of the body by providing support specifically to the lumbar to help maintain good posture during exercise or work.

It is a different object of this invention to provide a wearable lumbosacral device that can be used with existing compatible weight/waist training devices or supplied as a complete system or kit.

It is another different object of this invention to provide a wearable lumbosacral support system and kit that includes interchangeable inserts capable of changing the dimension and intensity of the support provided by the device.

It is a separate object of this invention to provide a method of use of the device and system disclosed herein, wherein said method improves the support delivered to the lumbosacral region of the body.

It is another, separate object of this invention is to provide an improved waist training belt capable of providing individualized, consistent, firm and comfortable pressure to the lumbosacral area of a wearer for support, weight training and therapeutic purposes.

REFERENCE CHARACTERS USED IN THE DRAWINGS

1. Stoling
2. Attachment band
3. Restraining strap
4. Lumbosacral insert
5. Wrap

BRIEF DESCRIPTION OF THE SEVERAL VIEWS OF THE DRAWING

The following figures form part of the specification and are included to further demonstrate certain aspects of the claimed subject matter, and should not be used to limit or define the claimed subject matter. The invention may be better understood by reference to one or more of the drawings in combination with the description of the embodiments presented. A more complete understanding of the present embodiments and further features and advantages thereof may be acquired by referring to the following description taken in conjunction with the accompanying drawings, in which like reference numerals may identify like elements, with the same or similar reference numerals.

FIG. 5 shows a cross sectional view of the lumbosacral insert positioned on the device.

FIG. 6 shows an embodiment of the device whereby a stoling is a separate component secured upon a wrap.

DETAILED DESCRIPTION OF THE INVENTION

While various embodiments are described herein, it should be appreciated that the present invention encompasses many inventive concepts that may be embodied in a wide variety of contexts. Illustrative embodiments of the invention are described below. Not all features of an actual implementation for all embodiments are necessarily described in this specification. In the development of any such actual embodiment, implementation specific decisions may be made to achieve the design specific goals, which may vary from one implementation to another. It will be appreciated that such a development effort would be a routine undertaking for persons of ordinary skill in the art having the benefit of this disclosure.

The device and method detailed in the following description and drawings provide a wearer with lumbar support while exercising or doing other activity that may push the lumbar out of its natural curve. The device comprises an adjustable wrap 5 extending around the body of the wearer; the wrap 5 is substantially a flexible belt or waist training device with a removeable contoured lumbar support section. The lumbar support can be inserted directly into restraining straps 3 attached to the wrap 5, or it can be connected to the wrap 5 by attachment of the stoling 1. The lumbar support can also be adjusted by removing and replacing the lumbar support components with differently sized supports to provide ample pressure or support relative to the need of the wearer. In a preferred embodiment, the removeable lumbar support is composed of foam or a foam core such that it is relatively rigid and non-collapsible, but the interstitial spaces in the foam or foam-like material provide for moderate reflexivity or flexion for comfort, since the device is worn against the wearer's body. In one embodiment the support is semi-circular and extends across the spine, interacting with the musculature of the back. The wrap 5 can be worn either over or under clothing. One skilled in the art would appreciate that various conforming and supporting shapes and dimensions of both the stoling 1 and the wrap 5 could be used to accommodate variously sized and shaped wearers, and still remain within the present disclosure.

Figure 1:
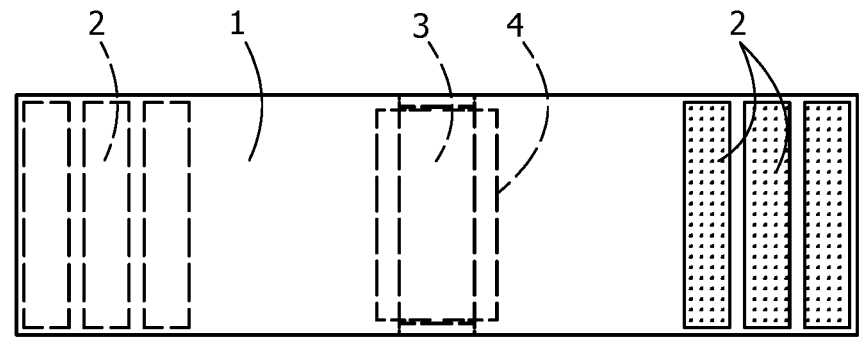
FIG. 1 is a top view showing a first side of the stoling portion of the invention.
Figure 2:
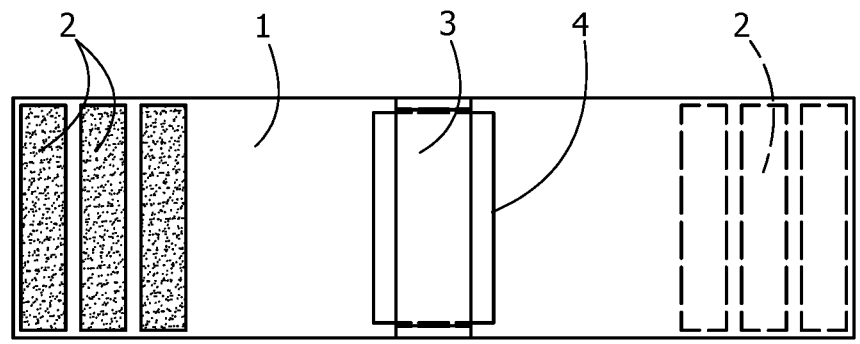
FIG. 2 is a view showing a second side of the stoling shown in FIG. 1.

In FIGS. 1 and 2, a first side and a second side, respectively, of the stoling 1 are shown. As seen in FIG. 1, the stoling 1 is a flexible casing or enclosure positioning and supporting the lumbosacral insert 4. In one embodiment, the stoling is made of fabric; fabric materials can include a variety of features based on wearer preference, such as waterproof, more or less elastic, colorful or plain, or could include indicia such as unique designs, trademarks, advertisements or sports logos. Such indicia may be printed, inlaid, dyed, airbrushed, embossed or otherwise affixed to one or both sides of the stoling 1 or the wrap 5. The stoling 1 comprises the first side, second side, a first end and a second end, and an attachment band 2 for securing it to itself and the wrap 5, so that it can extend around the wrap 5, and attach to itself, or directly to the wrap 5, to secure it in position thereon. The attachment band 2 can comprise dual lock tape, Velcro, hooks, snaps or other fastening components capable of releasably securing the stoling 1 around the wrap 5 in order to position the lumbar support. In a preferred embodiment, a wide band of Velcro or similar dual lock fabric fastening material is used. The attachment band 2 can be sewn, heat sealed, glued or otherwise attached permanently to the stoling 1. Variously positioned attachment bands 2 allow for adjustment in stoling 1 or wrap 5 size and contour; the embodiment shown in FIGS. 1 and 2 show three strips of interlocking attachment bands 2 connected securely to a first side (FIG. 1) and a second side (FIG. 2). In FIGS. 1 and 2, the attachment bands 2 drawn on the first end and second end of the stoling are shown with different patterns to indicate matingly conforming hook and loop portions of the attachment bands 2. Dotted lines are provided to show environmental features on the opposite side of the stoling 1 only, and form no part of the invention.

The stoling 1 also comprises an area that conforms to and provides a secure housing for the lumbosacral insert 4. It is traversed by the flexible or reflexive restraining strap 3 capable of expanding to allow the lumbosacral insert 4 to be placed within the area and returning to its original conformation around the lumbosacral insert 4, securing the lumbosacral insert 4 in place. In one embodiment, soft and flexible fabric material is used for the stoling 1 material and indicia is printed, screened or sewn onto the stoling 1. The restraining strap 3 comprises a strip of elastic fabric sewn, glued or heat sealed in place across the stoling. Alternatively, a pouch or pocket could be used to position the lumbosacral insert 4 and keep it secured in place on the device. In addition, one or more pockets capable of securely storing personal items such as keys, cell phone, or small note pad could be sewn, glued or heat sealed to the wrap 5 as an additional feature.

In FIG. 2, a view of the second side of the stoling 1 is shown. The attachment band 2 may include a strip of Velcro or similarly releasably adhering material, or areas or patches of dual lock tape or other attachment material as described above. The stoling 1 comprises one or more attachment bands 2 capable of securing the stoling 1 around or upon a wrap 5 in order to position the lumbosacral insert 4 across the lumbosacral region of a wearer's body to provide musculoskeletal support. One or more sides of the stoling 1 and one or more sides of the wrap 5 can also feature indicia such as trademarks, logos or personal messages.

Figure 3:
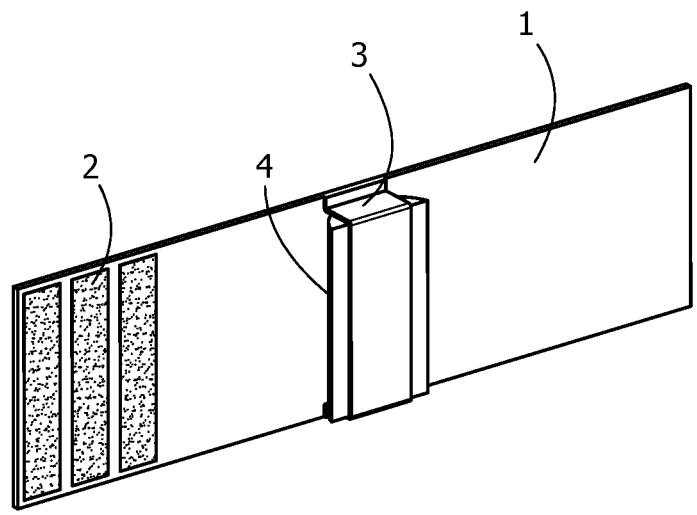
FIG. 3 is a perspective view of the stoling with the insert in position under the restraining strap.

FIG. 3 shows a perspective view of the stoling 1 of the device. In one embodiment, the stoling 1 is capable of securing to itself around the wrap 5; in this embodiment, attachment bands 2 on a first end of the stoling 1 on a first side of the stoling 1 can adhere or attach to attachment bands 2 on a second end of the stoling 1 on a second side, such that it is capable of both releasably encircling and connecting to itself around the wrap 5. In this way, the stoling 1 can be used with commercially available waist training devices. The restraining strap 3 can be secured to the stoling 1 in a lengthwise (meaning parallel with the long sides of the stoling 1) or widthwise (parallel with the shorter sides of the stoling 1) configuration in order to support and retain the lumbosacral insert 4. Also, the lumbosacral insert 4, which in a preferred embodiment has a flat side and a rounded side, can be positioned with the flat side against the stoling 1, as shown in FIG. 3 or the rounded side against it. In this way, the stoling 1 can be positioned around the wrap 5 with the ends of the stoling 1 folded around the first side of the wrap 5, or around the second side of the wrap 5, providing the wearer with more or less padding as desired to address specific physical needs. FIG. 6 further illustrates an embodiment of the assembled device as it engages with the wearer.

Figure 3A:
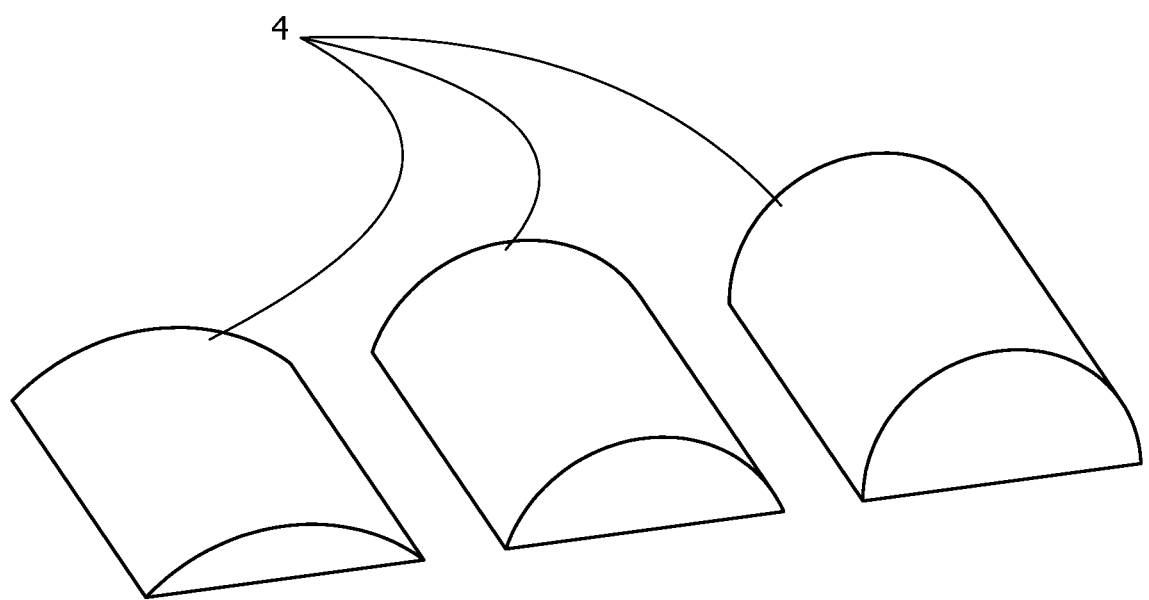
FIG. 3(a) is an illustration showing differently sized lumbrosachral insert components.

Alternatively, the attachment bands 2 on the first end, the second end or on both ends of stoling 1 can attach releasably to attachment bands 2 on the wrap 5 when the stoling 1 is positioned around the wrap 5. In this embodiment, the stoling 1 is releasably attached directly to the wrap 5 by connecting with an attachment band 2 positioned upon the wrap 5 lengthwise, meaning parallel with the long sides of the wrap 5, such that the stoling 1 is connected with and configured over and around the wrap 5 to add padding for comfort to the device around where the device contacts the wearer's body. In FIG. 3(a), various sizes of the lumbrosachral insert 4 are shown. The size of the insert can be changed to suit individuals of various sizes; the interchangeability of the size is also an important functional feature, as the size of the lumbosacral insert 4 can be reduced as healing or strengthening occurs. In a preferred embodiment, the lumbosacral insert 4 has a first rounded surface and a second flat surface, such that the flat surface is positioned against the wrap 5, and the rounded surface is positioned facing the wearer's body. One or more restraining straps 3 position and secure the lumbosacral insert, and further comprise elastic material capable of stretch and recoil, sized and positioned to matingly conform to and secure the lumbosacral insert.

FIGS. 4 (a-c) provide an illustration of an embodiment of the wrap 5. In a preferred embodiment, the wrap 5 comprises a first side and a second side and a first end and a second end, and a plurality of attachment bands 2 that are positioned on the wrap 5 on the first side or the second side at the first end and the second end so that it can be adjusted to make the device fit tighter or more loosely against the body by changing the fastening position of the attachment bands 2 that position the wrap 5 around the wearer's body. The attachment bands 2 are positioned on the wrap 5 so that it can be adjusted to make the device fit tighter or more loosely against the body by changing the fastening position of the attachment bands 2 that position the wrap 5 around the wearer's body. The fastening position is changed by pulling a first end of the wrap 5 away from the body, wrapping it around the body more or less tightly and connecting an attachment band 2 on a first side of the wrap 5 with the conforming attachment band 2 on a second side of the wrap 5. The second side connects and attaches with the first side of the attachment band 2. In one embodiment, attachment bands are Velcro or substantially similar hook and loop fastener strips. The wrap 5 is placed around the wearer's waist such that a lumbosacral insert 4 is then positioned against the lumbosacral area of the wearer's body, and fastened thereon with the attachment bands 2 appropriately positioned around the body.

Figure 4A:
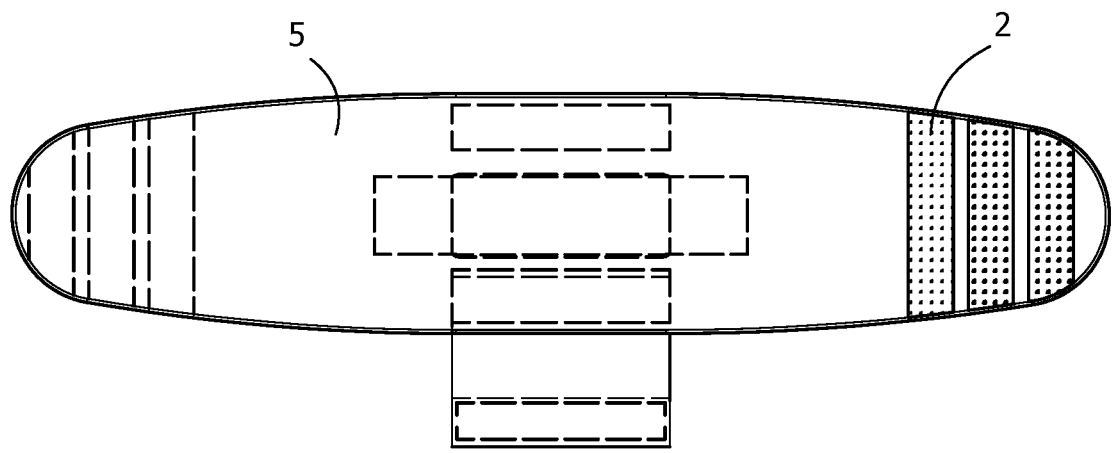
FIG. 4(a) is a view showing a first side of the wrap in an alternate embodiment of the invention wherein the stoling attaches directly to the wrap.
Figure 4B:
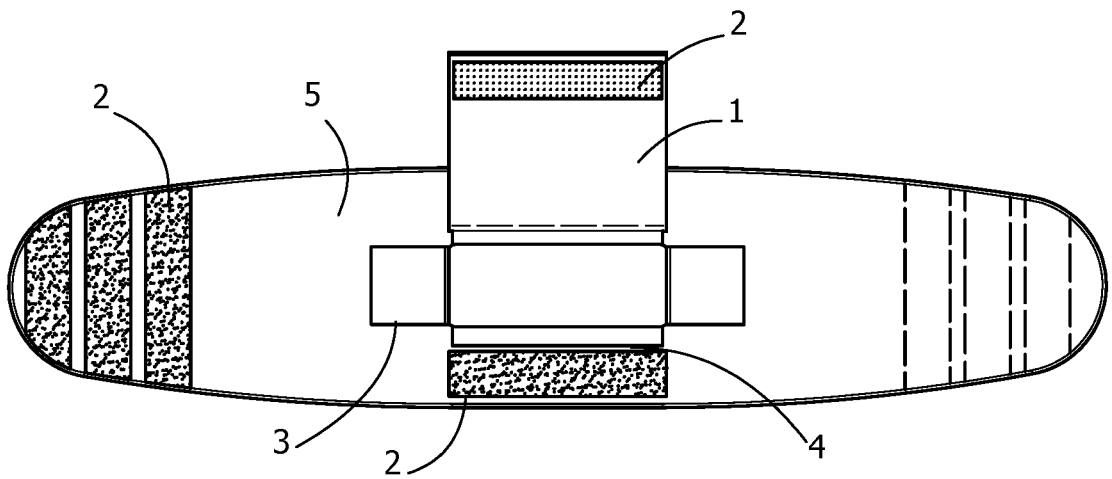
FIG. 4(b) shows the second side of the wrap shown in FIG. 4(a).
Figure 4C:
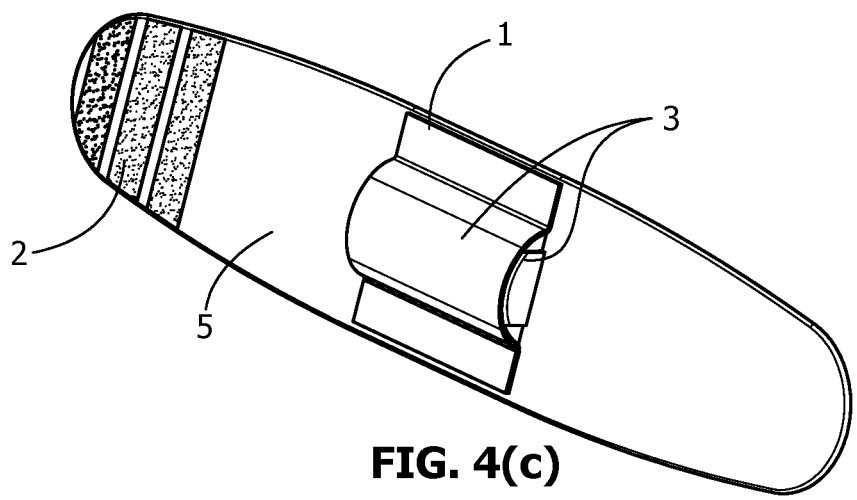
FIG. 4(c) is a perspective view of the embodiment shown in FIGS. 4(a) and 4(b).
Figure 7A:
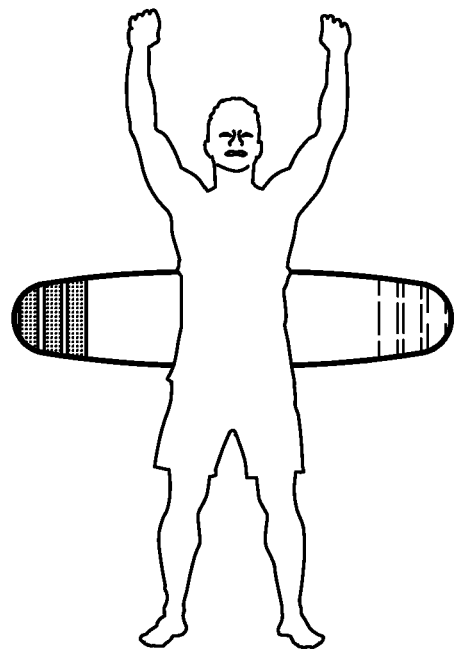
FIGS. 7(a-d) show the device positioned on a wearer and illustrates the method of use.
Figure 7B:
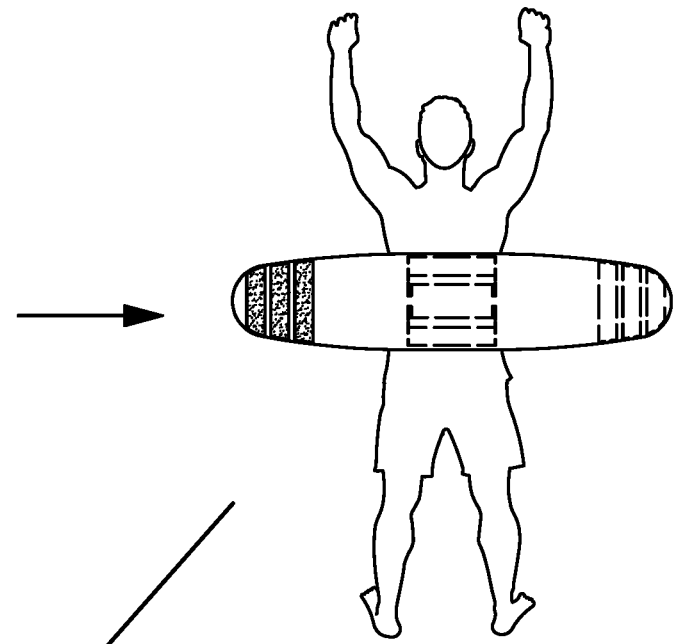
Figure 7C:
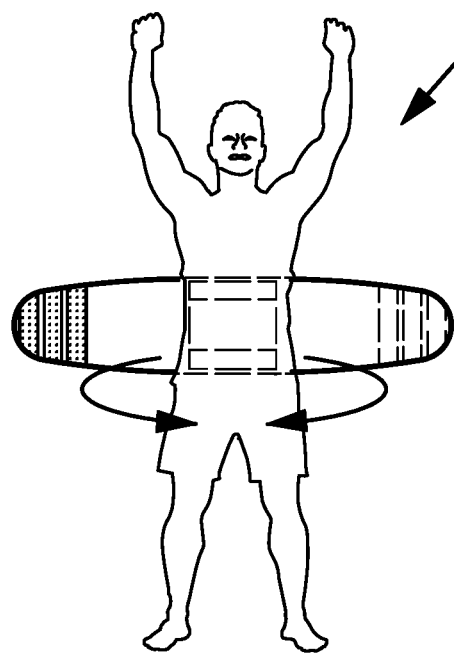
Figure 7D:
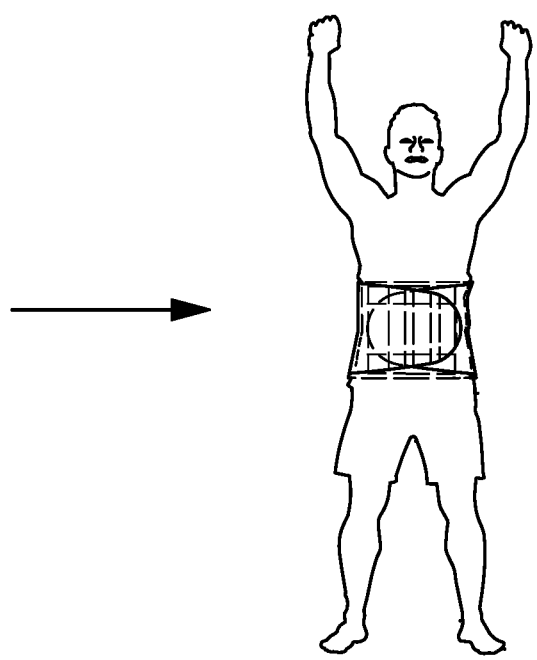

In FIG. 4(a), a first side of an embodiment of the wrap 5 is shown. The wrap 5 can be shaped and sized to fit any wearer, but typically could be made in a set of sizes (small, medium, large, extra-large) that can be adjusted to make the device fit tighter or more loosely against the body by changing the fastening position. The wrap 5 comprises elastic fabric or other material capable of stretch and recoil to its original conformation, and one or more attachment bands 2 to position the wrap 5 around the wearer's body. In one embodiment, the fabric or material comprising the wrap 5 would also include one or more functional features which could include but are not limited to lightweight, breathable (capable of air exchange) and water-resistant. The wrap 5 also includes one or more attachment bands 2 and one or more restraining straps 3 or pockets capable of holding one or more lumbar support inserts 4 securely. Attachment bands 2 connected to the wrap 5 can be sized, shaped and positioned upon the wrap in various locations, including but not limited to either end of the wrap 5 as depicted in FIG. 4; the dotted lines represent environmental features, and form no separate part of the invention. The device may be easily assembled and prepared for use by placing the stoling 1, wrap 5, and lumbosacral insert 4 on a flat surface. The wrap 5 is positioned with a first side facing down and a second side facing up as shown as in FIG. 4(b). A lumbosacral support 4 of the desired size is placed within the restraining strap 3 centered upon the wrap 5. The stoling 1 is then secured around the lumbosacral insert 4, as shown in FIG. 4(c).

FIG. 4(b) shows a second side of the embodiment of the invention shown in FIG. 4(a), wherein the stoling 1 is releasably attached directly to the wrap 5. The stoling 1 in this embodiment is shorter in length than the stoling embodiment that is described in FIG. 3, and is connected directly to the wrap 5 via an attachment band 2 positioned lengthwise on the wrap 5. Restraining straps on either the stoling 1 or the wrap 5 secure the lumbosacral insert 4; in this way the stoling is configured over and around the restraining strap 3 and insert 4 positioned therein to add additional security and padding or comfort to the device around where the device contacts the wearer's body. FIG. 4(c) shows a perspective view of this embodiment of the invention.

FIG. 5 shows a cross sectional view of the lumbosacral insert 4 positioned on the device. The lumbosacral insert 4 is releasably secured by a restraining strap 3; the restraining strap 3 is either attached directly to the wrap 5 as shown in FIGS. 4(a-c) or to the stoling 1. The stoling 1 is then attached to the wrap 5 via attachment bands 2 positioned lengthwise, meaning along a long side of the wrap 5 as illustrated in FIG. 4, or wrapped around the wrap 5 as shown in FIG. 6, in order to secure the lumbosacral insert 4 in position.

FIG. 6 shows a diagram of the invention and it's method of use, whereby the stoling 1 is separately secured to the wrap 5 by attaching and securing to itself. The lumbosacral insert 4 is secured by the restraining strap 3 against the stoling 1. The stoling 1 is then positioned around the wrap 5 and releasably secured thereon. The wrap 5 is now ready for positioning around the wearer's body, as illustrated in FIG. 7.

FIGS. 7(a-d) show the device positioned on a person wearing it (the wearer) and illustrates the method of using the invention. As depicted in this figure, attachment bands 2 are connected to the wrap; they can be sized, shaped and positioned upon the wrap 5 in various locations, including but not limited to either end of the wrap; the dotted lines in this figure represent environmental features, and form no separate part of the invention.

Once the device is assembled, it can be positioned upon the wearer. The wrap 5 is releasably positionable upon a wearer, and is capable of conforming to the stoling 1; the stoling 1 can be moveably adjusted and secured around the wrap 5 to position the lumbosacral insert 4 against the lower back area of the wearer's body.

The wrap 5 is positioned around the wearer's waist, and releasably secured thereon, such that the rounded surface of the lumbosacral insert 4 is facing and positioned against the wearer's body perpendicular to the spine. The flexible and reflexive nature of the wrap 5 allows the wearer to stretch the wrap 5 around the body in order to tightly position the device thereon, with the lumbosacral insert 4 centered on and in contact with the wearer's lumbar region of the back at the top of the hips. The device is then secured to the wearer's body by releasably attaching the wrap 5 by connecting attachment bands 2 on a first end of the wrap 5 with attachment bands 2 on a second end of the wrap 5.

The lumbar region of the body is supported by the device during physical activity. Once activity is complete, the device can be removed from the body by releasing or uncoupling the attachment bands 2 of the wrap 5 and removing it from the body. It can then be rolled or folded and stored within a carrying case with replacement or variously sized lumbosacral inserts for future use.

The invention claimed is:

1. A device for providing support to a lumbosacral region of a body of a wearer, comprising:
    a. a stoling comprising a longitudinal length, further comprising at least a first side and a second side and at least a first longitudinal end and a second longitudinal end; a restraining strap capable of receiving and securing at least one lumbosacral insert; and one or more attachment bands positioned on one or both longitudinal ends of the first side and the second side capable of releasably securing the stoling around or upon a wrap in order to position the at least one lumbosacral insert across the lumbosacral region of the wearer's body to provide musculoskeletal support;
    b. the at least one lumbosacral insert sized to fit within the restraining strap, and capable of being secured by the restraining strap, wherein the restraining strap does not completely enclose the at least one lumbosacral insert and stretches and recoils to matingly conform to differently sized lumbosacral inserts; and
    c. a wrap comprising a longitudinal length and lateral width that is releasably positionable upon the wearer; wherein the stoling wraps around the lateral width of the wrap such that the longitudinal length of the stoling extends perpendicularly to the longitudinal length of the wrap to position the at least one lumbosacral insert between the wrap and the stoling, wherein the stoling can be moveably adjusted and removably secured around or upon the wrap to position the at least one lumbosacral insert against a lower back area of the wearer's body, such that the wrap is usable independently of the stoling.

2. The device of claim 1, wherein the wrap further comprises elastic fabric capable of stretch and recoil to its original conformation.

3. The device of claim 2, wherein the fabric of the wrap is lightweight, capable of air exchange and water-resistant.

4. The device of claim 1, wherein the restraining strap further comprises elastic material.

5. The method of using the device of claim 4, further including the step of positioning the at least one lumbosacral insert upon the stoling by first securing it thereon with the restraining strap, then securing the stoling to the wrap by wrapping the stoling around the wrap and attaching the stoling to itself via the one or more attachment bands.

6. The device of claim 1 wherein the stoling is configured over and around the wrap to add padding for comfort to the device at a location where the device is configured to contact the wearers body, and the at least one lumbosacral insert is configured to be positioned across a back of the wearer perpendicular to the spine.

7. The device of claim 1 wherein the stoling is releasably attached to itself around the wrap by connecting the one or more attachment bands secured on the first longitudinal end of the stoling to the one or more attachment bands on the second longitudinal end of the stoling so that the stoling is capable of releasably encircling and thereby connecting to the wrap.

8. The device of claim 1 wherein the stoling further comprises soft and flexible fabric material.

9. The device of claim 1 wherein the stoling, the wrap, or both include indicia.

10. The device of claim 1 wherein the wrap comprises a first side and a second side and a first end and a second end, and a plurality of attachment bands are positioned on the devise wrap on the first side or the second side at the first end and the second end so that the wrap can be adjusted to make the device fit tighter or more loosely against the body by changing a fastening position of the plurality of attachment bands that position the wrap around the wearer's body.

11. The device of claim 1, wherein the at least one lumbosacral insert further comprises a first rounded surface and a second flat surface, such that the flat surface and the rounded surface are moveably positioned against the wrap or the stoling to place the rounded surface facing the wearer's body.

12. The device of claim 1, wherein the at least one lumbosacral insert further comprises a water-repellant foam material that is firm to add support but capable of minor compression and expansion for comfort when positioned against the body.

13. The device of claim 1, wherein the restraining strap comprises a strip of elastic fabric sewn, glued or heat sealed onto the stoling in a location traversing an area occupied by the at least one lumbosacral insert on the stoling.

14. The device of claim 1 further comprising one or more pockets on the wrap capable of securely storing personal items.

15. A method of using the device of claim 1 comprising the steps of:

i. assembling the device by placing the stoling, wrap, and at least one lumbosacral insert on a flat surface and positioning the wrap with a first side facing down and a second side facing up;
    ii. placing the at least one lumbosacral support of a desired size within the restraining strap and centered upon the wrap;
    iii. securing the stoling around the wrap;
    iv. releasably positioning the assembled device upon the wearer and moveably adjusting and securing the wrap to position the at least one lumbosacral insert against the lower back area of the wearer's body such that a rounded surface of the at least one lumbosacral insert is facing and positioned against the wearer's lumbar region of the body to support the wearer during physical activity;
    v. once the physical activity is complete, the device is removed from the body by releasing or uncoupling attachment bands of the wrap and removing the wrap from the body; and
    vi. rolling or folding the device and storing it within a carrying case with replacement or variously sized lumbosacral inserts for future use.

16. A kit for providing support to a lumbosacral region of a body, comprising the device of claim 1 including the wrap, stoling, and a plurality of differently sized lumbosacral inserts; and a carrying case for storing and transporting the device.

* * * * *